(12) United States Patent
Haselhurst et al.

(10) Patent No.: US 7,788,343 B2
(45) Date of Patent: Aug. 31, 2010

(54) METHOD AND SYSTEM FOR ANALYSIS OF MEDICAL DATA

(76) Inventors: Patrick Haselhurst, 183 rue Osborne, Saint-Lambert, QC (CA) J4R 1B3; Jeremy Brouillette, 4336 Marcil Avenue, Quebec, QC (CA) H4A 2Z8

( * ) Notice: Subject to any disclaimer, the term of this patent is extended or adjusted under 35 U.S.C. 154(b) by 457 days.

(21) Appl. No.: 11/540,666

(22) Filed: Oct. 2, 2006

(65) Prior Publication Data

US 2008/0082659 A1 Apr. 3, 2008

(51) Int. Cl.
*G06F 15/173* (2006.01)
(52) U.S. Cl. .................................................. 709/219
(58) Field of Classification Search .............. 709/219; 705/2; 382/276
See application file for complete search history.

(56) References Cited

U.S. PATENT DOCUMENTS

| | | | |
|---|---|---|---|
| 6,112,224 A | 8/2000 | Peifer et al. | |
| 6,260,021 B1 | 7/2001 | Wong et al. | |
| 6,409,660 B1 | 6/2002 | Sjöqvist | |
| 6,454,708 B1 | 9/2002 | Ferguson et al. | |
| 6,705,990 B1 | 3/2004 | Gallant et al. | |
| 6,985,762 B2 | 1/2006 | Brashears et al. | |
| 2002/0010679 A1 | 1/2002 | Felsher | |
| 2003/0101076 A1* | 5/2003 | Zaleski | 705/2 |
| 2004/0039261 A1* | 2/2004 | Bardy | 600/300 |
| 2004/0073098 A1 | 4/2004 | Geva et al. | |
| 2004/0240752 A1* | 12/2004 | Dobbs et al. | 382/276 |
| 2005/0010087 A1 | 1/2005 | Banet et al. | |
| 2005/0021370 A1 | 1/2005 | Riff et al. | |
| 2005/0108057 A1* | 5/2005 | Cohen et al. | 705/3 |
| 2005/0113650 A1 | 5/2005 | Pacione et al. | |
| 2005/0135306 A1 | 6/2005 | McAllen et al. | |
| 2005/0171411 A1* | 8/2005 | KenKnight et al. | 600/300 |
| 2006/0017579 A1 | 1/2006 | Albert et al. | |
| 2006/0074709 A1 | 4/2006 | McAllister | |
| 2006/0155579 A1* | 7/2006 | Reid | 705/2 |
| 2008/0004904 A1* | 1/2008 | Tran | 705/2 |

FOREIGN PATENT DOCUMENTS

| | | |
|---|---|---|
| CN | 1618395 | 5/2005 |
| EP | 1097671 | 5/2001 |
| WO | WO03043494 | 5/2003 |
| WO | WO2004002301 | 1/2004 |

* cited by examiner

*Primary Examiner*—Wing F Chan
*Assistant Examiner*—Tesfay Yohannes
(74) *Attorney, Agent, or Firm*—Bereskin & Parr LLP/S.E.N.C.R.L., s.r.l.

(57) ABSTRACT

A system for analyzing medical data is provided for. The system comprises a server adapted to be connected to a communication network for storing medical data, wherein the medical data is generated by a medical device; a session manager for establishing an authenticated session for a user to communicate with the server; and a data manager connected to the session the data manager allowing for storage of said medical data and providing access to previously stored medical data.

17 Claims, 13 Drawing Sheets

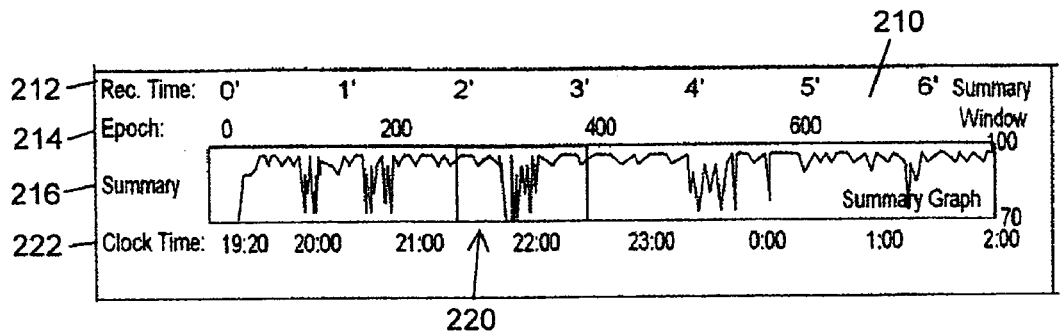
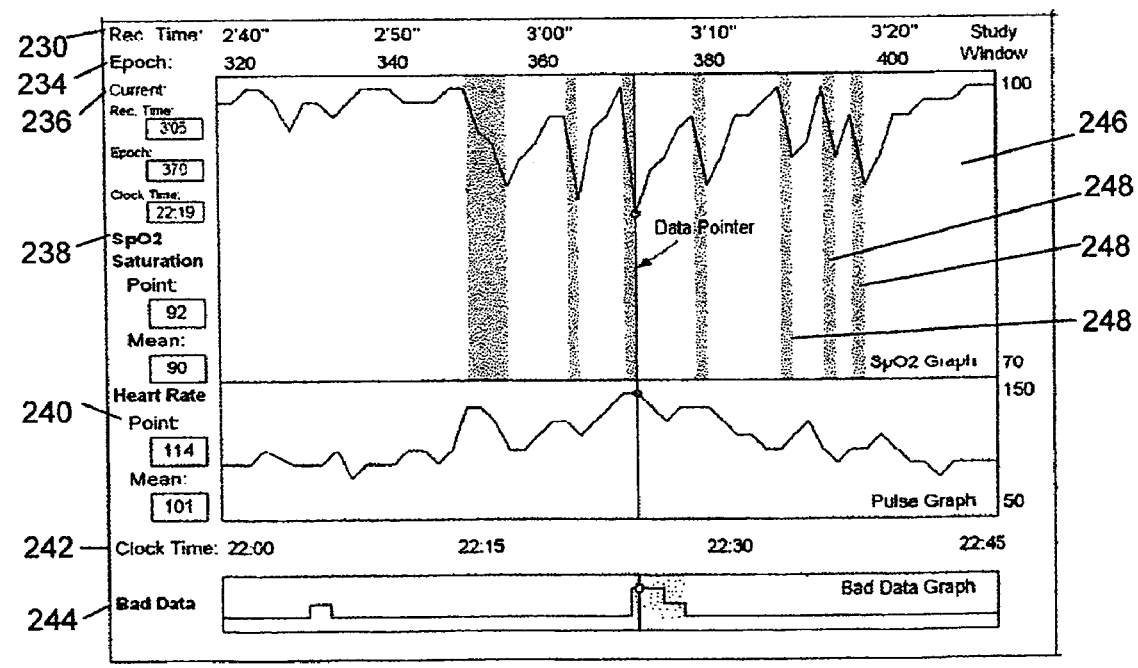
FIG. 8

Study Data Window Ref#: 4 — 270, 272

Length of Recording (min): 380 — 274

Length of Good Data (min): 372 — 276

---

Study Summary — 280

Baseline SaO2: 102 — 282
Min SaO2: 140 — 284

| | # Desats | % REC time in desat |
|---|---|---|
| <90 | 5 | 0.9 |
| <85 | 2 | 0.2 |
| <80 | 1 | 0.1 |
| <70 | 0 | 0 |

— 286 # of Clusters: 3 — 288

Min Pulse: 102 — 290
Max Pulse: 140
Mean Pulse: 121

View Controls: [View Study] [◁ Page ▷] — 292

Bad Data
Bad Data Type: drop >= 5% in 2s — 294

FIG. 9

METHOD AND SYSTEM FOR ANALYSIS OF MEDICAL DATA

FIELD OF THE INVENTION

The invention relates generally to the analysis of data from medical devices, and more specifically to systems and methods for manual and automated analysis of medical data.

BACKGROUND OF THE INVENTION

Medical devices are used by patients to monitor aspects of their health. Most patients visit their health professionals on a regular basis, particularly when they require health studies to be conducted. Often, under the supervision of a health professional the patient will engage a medical device that will collect readings, and those readings are then interpreted by the health professional.

When engaging the medical device, there is often very little interaction with the health professional. The patient is generally able to engage some medical devices without need for a health professional. However, as the health professional is required to review the results of the monitoring, the patient most often is required to attend a clinic in order to use such medical devices.

SUMMARY OF THE INVENTION

In a first aspect of the invention, a system for analyzing medical data is provided for. The system comprises a server adapted to be connected to a communication network for storing medical data, wherein the medical data is generated by a medical device; a session manager for establishing an authenticated session for a user to communicate with the server; and a data manager connected to the session, wherein the data manager allows for storage of the medical data and provides access to previously stored medical data; a medical data analyzer connected to the data manager for analyzing the medical data and providing visual representations thereof.

In a second aspect of the invention, a system for analyzing medical data is provided. The system comprises a medical device recording medical data from a patient over time; a server connected to a communication network for storing the medical data; a data manager associated with the medical device for establishing an authenticated session over the communication network with the server to enable the server to control further use of the medical data; and a medical data analyzer having at least one component associated with the server to allow a medical professional controlled access to the medical data, wherein the medical data analyzer analyzes the medical data.

BRIEF DESCRIPTION OF THE DRAWINGS

For a better understanding of embodiments of the systems and methods described herein, and to show more clearly how they may be carried into effect, reference will be made by way of example, to the accompanying drawings in which:

FIG. 8 is a sample illustration of a study window and a summary window;

FIG. 9 is a sample illustration of a study data window and a study summary window;

DETAILED DESCRIPTION OF THE INVENTION

Figure 1:
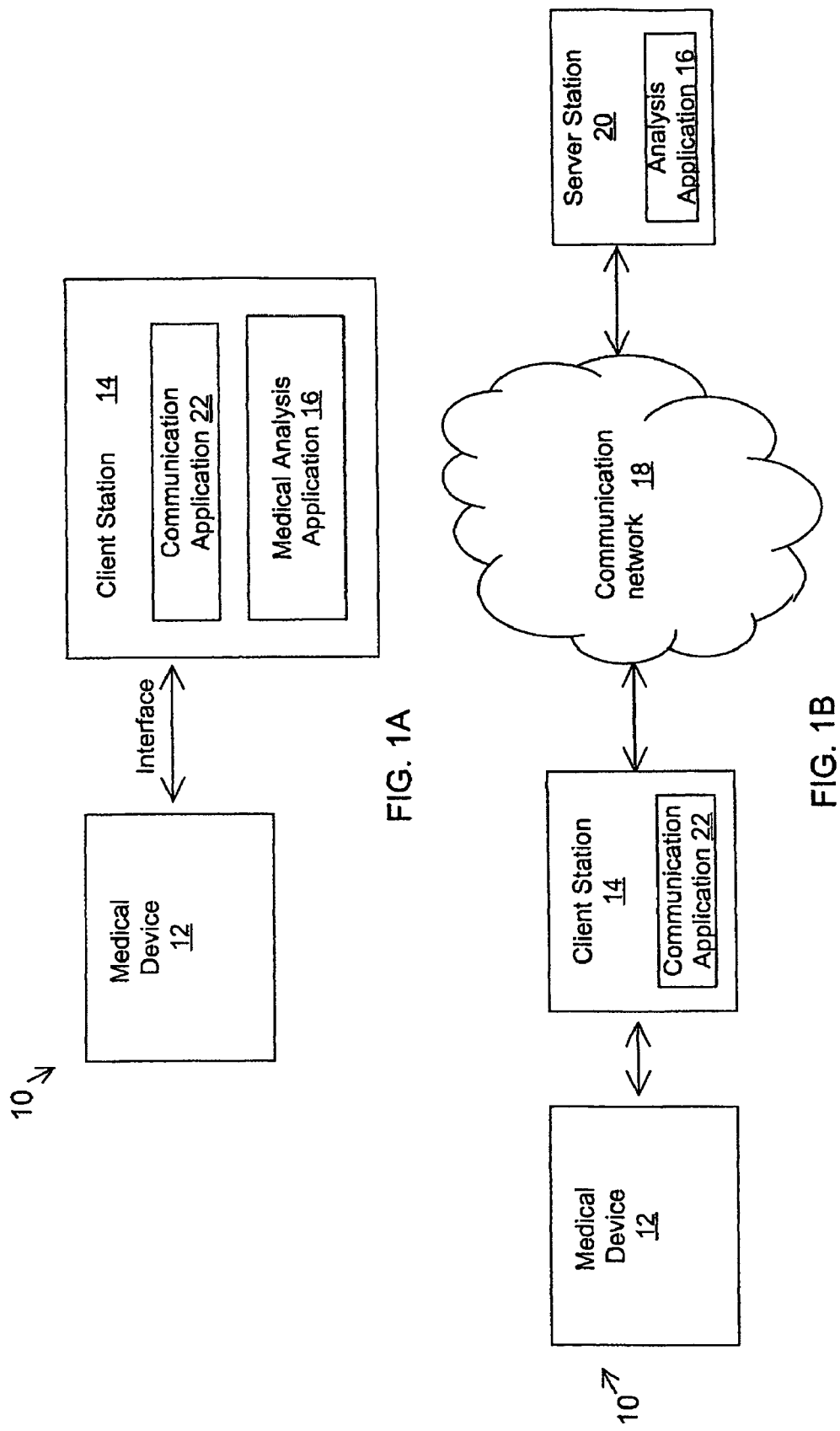
FIG. 1A is a block diagram of the interaction between a medical device and a client station.
FIG. 1B is a block diagram of the interaction between a medical device, a client station, and a communication network.

Reference is now made to FIG. 1A-1B, where components of a medical device analysis system 10 are shown in an exemplary embodiment. The medical device analysis system 10 as described in detail below, is used to monitor one or more physiological parameters, analyze data, and store data from medical devices that are used for patient monitoring. The medical device 12 communicates with a client station 14 through an interface as is described in detail below. The client station 14 has resident upon it, or accessible to it, a medical analyzer application 16, and a communication application 22.

The medical devices 12 are used to measure one or more physiological parameters associated with a patient. The medical devices 12 may be used to monitor physiological parameters that include, but are not limited to, pulse, blood oxygen levels, arterial oxygen saturation, arterial pluse waveform, pre pulse rate, breath rate, ecg, inspiratory flow, expiratory flow, tidal volume, rib cage excursions, abdomen excursions, methemoglobin, carboyhemoglobin, and oyhemoglobin. The medical devices 12 are engaged by the patient in order to monitor physiological parameters. Medical devices 12 may include, but are not limited to, pulse oximeters, electronic stethoscopes, ECG monitors, electronic weighing scales, glucose meters, respirators and electronic blood pressure monitors. For purposes of the description, the system 10 and the medical device 12 will be described with reference to a pulse oximeter. A pulse oximeter monitors a patient's blood gas. However, the system 10 may be used with any medical device 12 that is able to measure physiological parameters and transmit the resulting data.

After the physiological parameters have been measured, the resulting medical data is uploaded from the medical device 12 to the client station 14. The upload of the medical data, in an exemplary embodiment, is managed by the communication application 22. In alternative embodiments, the upload of the medical data may be managed by the medical device 12. The use of a medical device 12 upon a patient to measure physiological parameters is referred to as a study. The term medical data is used to refer to data representative of the measurement of physiological parameters. The client station 14 is a computing device that is able to interface with the medical device 12 and receive data from the medical device 12 and is described in further detail below. The client station has resident upon it, or accessible to it, a medical analysis application 16 and a communication application 22. The medical analysis application 16 is used to receive, store, retrieve, and analyze the medical data as described below. The analysis application 16 analyzes the medical data through use of analysis algorithms that may be modified by the user. The communication application 22, in an exemplary embodiment is used to manage the transfer of medical data from the medical device 12 to the client station 14. The communication application 22 ensures that the medical data is transmitted to the analysis application 16, so that the medical data may be analyzed appropriately. As the system 10 may be used with any medical device 12, the medical data may represent various types of readings, including but not limited to pulse readings, and blood oxygen readings. The client station 14 may be any type of computing device, including, but not limited to a personal computer, laptop computer, slim line computer, or dedicated kiosk computer. The analysis application 16 receives the medical data and proceeds to analyze the data as is described in detail below.

The users of the system include patients and medical professionals. Patients engage the system 10 to have the data from their medical device 12 stored and analyzed. The medical professionals, who include, but are not limited to physicians, nurses, researchers and other trained individuals, engage the system 10 to review the results of the analysis, and to aid in the conduction of the analysis. The medical professionals may correspond with one another and with the patient regarding the study, both on-line in a collaborative session, and in non-collaborative sessions.

The system 10 as described with reference to FIG. 1A, is described with respect to one configuration of components. Reference is now made to FIG. 1B, where another embodiment of an analysis system 10 is shown. In this embodiment, the medical device 12 interfaces with the client station 14, and the client station has resident upon it, or accessible to it, a communication application 22. The client station 14 communicates with a communication network 18. The communication network 18 may be any network that allows for the transmission of data. The communication network 18 may include, but is not limited to, the Internet, the Intranet, a wide area network, a local area network, and a fiber channel network. The client station 14 transmits data that has been received from a medical device 12 through the communication network 18 to a server station 20. The server station 20 has accessible to it, or resident upon it, the analysis application 16. The communication application 22 may be used to access the server station 20. In an exemplary embodiment, the communication application 22 is an applet that provides the user with functionality that allows the user to communicate with the server station 20. The communication application 22, in an exemplary embodiment displays the graphical representations of the medical device data that has been analyzed. The communication application 22, in an exemplary embodiment has functionality that allows for the establishment of authenticated sessions as described below, and for the analysis of medical data.

Figure 2:
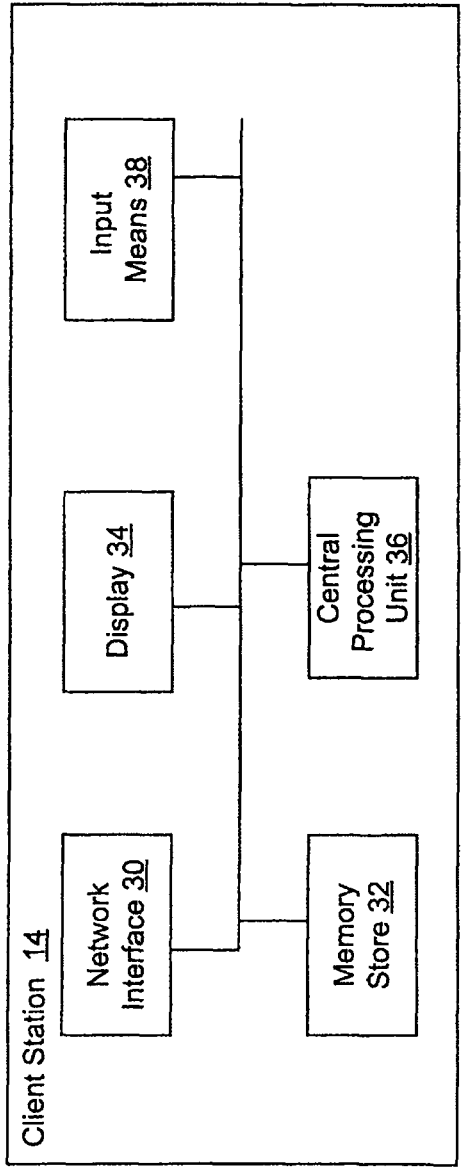
FIG. 2 is a block diagram of the components of a client station.

Reference is now made to FIG. 2, where the components of a client station 14 are shown in one exemplary embodiment. The client station 14, in an exemplary embodiment, has associated with it a network interface 30, a memory store 32, a display 34, a central processing unit 36, and input means 38.

The network interface 30 enables the respective station to connect to the communication network 18. The network interface 30 may be a conventional network card, such as an Ethernet card, wireless card, or any other means that allows for communication with the communication network 18. The memory store 32 is used to store executable programs and other information, and may include storage means such as conventional disk drives, hard drives, CD ROMS, or any other non volatile memory means. The display 34 provides a visual interface to display information to the user of the client station 14 upon a monitor type device. The central processing unit (CPU) 36 is used to execute instructions and commands that are loaded from the memory store 32. The input means 38 allows users to enter commands and information into the respective station. Client stations 14 may have associated with them one or more input means 38, which may include, but are not limited to, any combinations of keyboards, pointing devices such as a mouse, or other means such as microphones.

Figure 3:
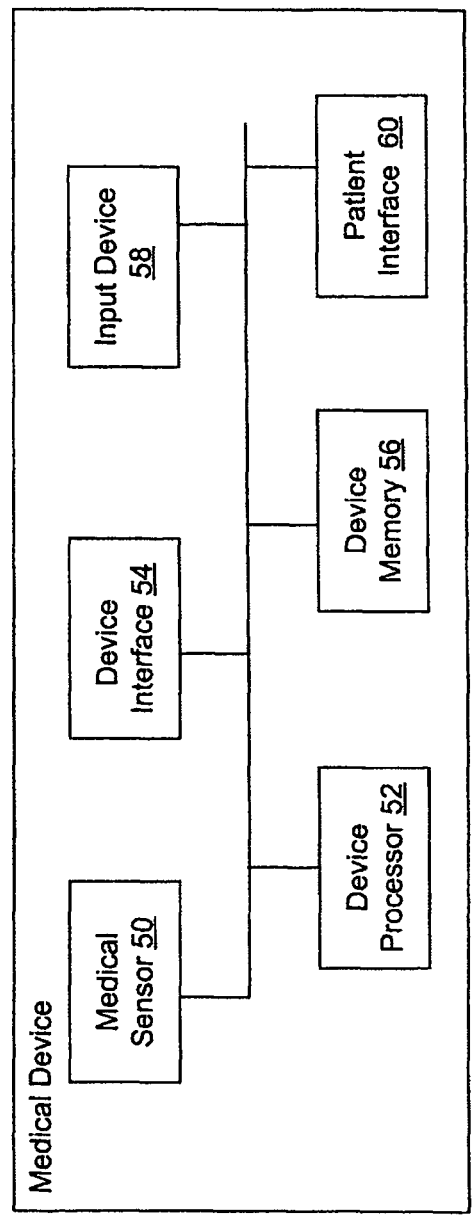
FIG. 3 is a block diagram of the components of a medical device.

Reference is now made to FIG. 3, where the components of a medical device 12 in an exemplary embodiment are shown. The components shown in FIG. 3 allow for measurements of physiological parameters and for transmitting the resulting data to external devices. In an exemplary embodiment, a medical device 12 may include, but is not limited to the following components, a medical sensor 50, a device processor 52, a device interface 54, a device memory 56, an input interface 58, and a patient interface 60. The medical sensor 50 measures one or more physiological parameters. Although various medical devices 12 may be used with the system 10, the system 10 is described with reference to a pulse oximeter. With a pulse oximeter, the medical sensor 50 provides a source of light at varying wavelengths. Due to the haemoglobin in the blood, the rate of light absorbtion differs based on the respective levels of saturation or desaturation. Based on the levels of light absorbtion at both wavelengths, the percentage of haemoglobin that is oxygenated is determined and recorded. The operation of the device sensor 50 depends on the physiological parameters that are being read, and the sensor 50 has been described here with respect to the detection of blood oxygenation levels for purposes of example. The device processor 52 processes the readings that are taken by the sensor 50. The device interface 54 provides a mechanism by which the device 12 is able to communicate with external devices. The device interface 54 allows for the medical data to be transmitted to computing devices for further processing as described below. In an exemplary embodiment, the device interface provides input and output capabilities. The device interface 54 may include, but is not limited to, a RS232 serial connection, USB, Bluetooth, disk, or wireless connection. The medical device data may be transferred in a variety of formats including those that are specific to the manufacturer of the medical device, and may also include, but are not limited to, serial or binary formats. The medical device data when transferred from the respective medical device will include, in an exemplary embodiment identifier information that is used to identify the particular medical device and/or user. Examples of such information may include, the service number of such a device or any other information that can identify the device and/or the patient. The device memory 56 is used to store instructions that are used by the device processor 52 and to store medical data as required. The device interface 54 transmits the medical device data to the client station 14, and more specifically, to the communication application 422. The communication application 422 translates the medical device data to a format that is suitable. The input device 58 provides the user of the medical device 12 with input mechanisms where they may input commands into the medical device 12. For example, the device interface may be a touch screen device or may be a set of buttons that allow for certain functionality of the device 12 to be activated. The device interface may also provide a display that the user may use when inputting any commands to the device 12. The patient interface 59 is used to engage the patient's body to be able to take readings of physiological parameters. The patient interface 59 may include a probe that is placed on a part of the body.

Figure 4:
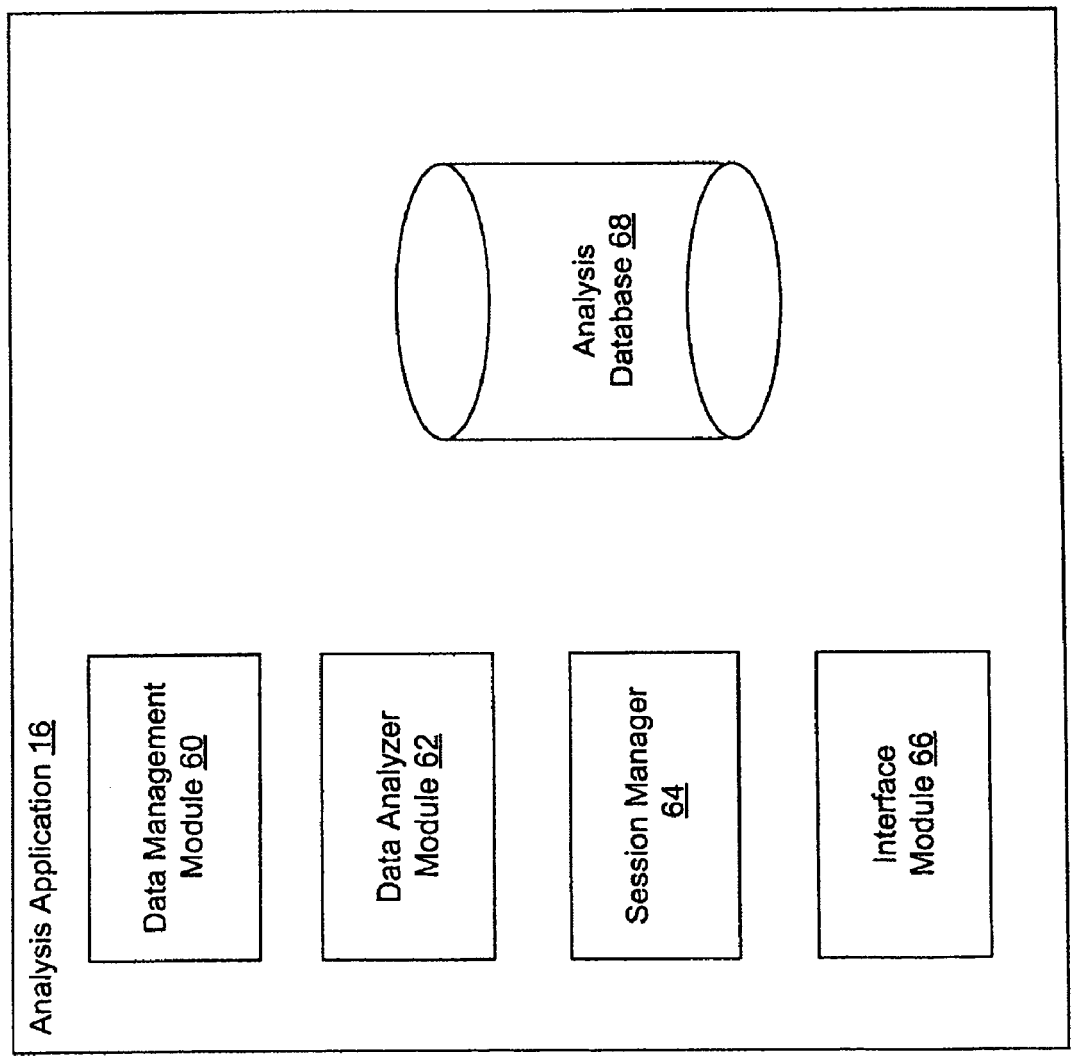
FIG. 4 is a block diagram illustrating the components of an analyzer application.

Reference is now made to FIG. 4, where the components of the analysis application 16 are shown in an exemplary embodiment. In an exemplary embodiment, the analysis application 16 comprises a data management module 60, a medical data analyzer module 62, a session manager 64, an interface module 66, and an analysis database 68. The data management module 60 manages the storage and retrieval of medical data and is herein referred to as a data manager. The medical data analyzer module 62 receives medical data that has been generated at a medical device 12 and proceeds to analyze the data, and is herein referred to as a medical data analyzer. The analysis of medical data is explained in further detail below. The session manager 64 establishes an authenticated and secure communication session between the client station 14 and a server 20. The interface module 66 allows the analysis application and its components to communicate with client stations 14. If the analysis application 16 is resident upon a client station 14, then the interface module allows the client station 14 to interface with the medical device 12. The interface module 66 also generates visual representations of the analysis that is conducted upon the medical data as described below. The analysis database 68 stores records of all users (patients and medical professionals) of the system 10, and the medical data, and analysis conducted upon the medical data.

The analysis application 16 may be deployed on either a server 20, or a client station 14 depending on the configuration of the components in the system 10. If the system 10 includes medical devices 12 that interact directly with a client station 14 and not through a communication network 18, the analysis application 16, and more specifically, the medical data analyzer proceeds to analyze the medical data at the client station 14. If the system includes a communication network 18, where the client stations 14 communicate with a server 20 through the communication network 18, the analysis application 16 operates upon the server station 20. In an exemplary embodiment, the client station 14 interacts with the server station 20 through the Internet. In an exemplary embodiment, the analysis application 16 is server based and receives data from the medical device and processes it upon the server 20 and displays representations of the analysis for viewing and interaction with the user through a web based interface.

Figure 5:
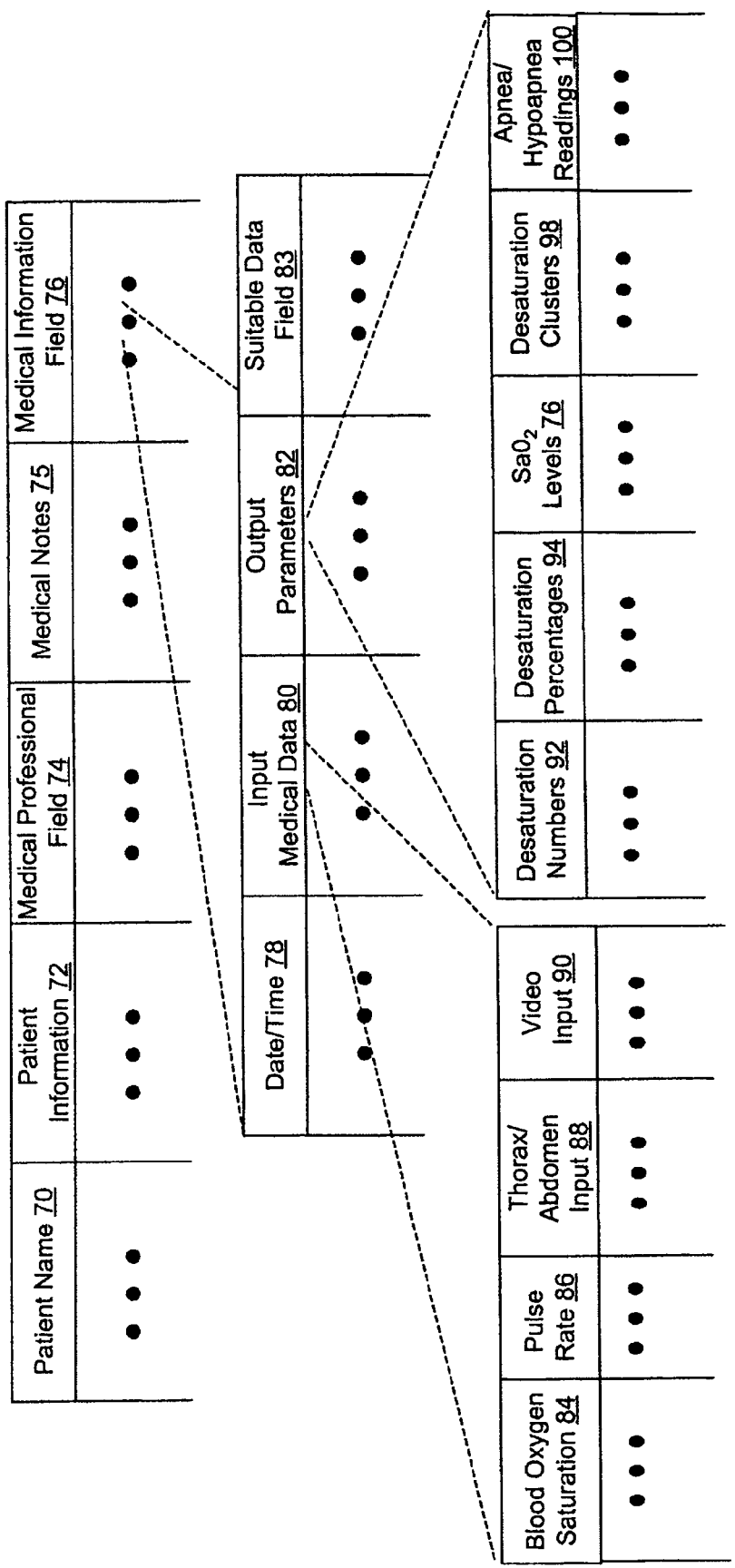
FIG. 5 is a block diagram illustrating the fields of an analysis database.

Reference is now made to FIG. 5, where the sample fields of an exemplary embodiment of the analysis database 68 are shown. The analysis database 68 has been shown as one database, however more than one database may be used. The analysis database 68 is used to store information regarding the patients and medical professionals who use the system and to store medical data. The medical device 12 provides medical data representative of physiological parameter readings taken during a study that will be referred to as medical data. The medical data may include, but is not limited to data associated with the following physiological parameters, the blood oxygen saturation levels, and the pulse rate. One or more medical devices 12 may be used to conduct a study. For example, video of a patient may be taken during a study and analyzed along with medical device data received from other devices. Based on the input medical data, the medical data analyzer proceeds to analyse the data and determines output parameters. The output parameters for example when using a pulse oximeter as an example, may include, but are not limited to, the number of desaturations, SaO2 levels, mixed obstructive apnea indexes and any other such parameters. As the medical device 12 is able to transmit data to a client 14 station in near real-time, the medical data analyzer, as is explained below, is able to process the data in real time and provides visual representations as the data is being analyzed. The analysis database 68 stores the results of the processing, so that it may be subsequently accessed by the patient or a medical professional. The medical professionals are able to analyze the data, and collaborate with other medical professionals by both reviewing, editing and revising the results of the study on at the same time.

As mentioned above, the fields of the analysis database 68 depend on the medical device 12 and the type of analysis that is being undertaken. For purposes of this example, as the pulse oximeter is being used as the medical device 12 the fields of the analysis database 68 are reflective of the analysis that is conducted upon data received from an oximeter. In an exemplary embodiment, the analysis database comprises the following fields, a patient name field 70, a patient profile field 72, a medical professional field 74, medical notes 75, and a medical information record 76.

The patient name field 70 stores the name of the patient or user of the system 10. The patient information field 72 stores information regarding the patient, which may include, but is not limited to, the address, date of birth, general health information, payment info, the name of a clinic or hospital that they may be affiliated with and other demographic information regarding the patient. The medical professional field 74 stores the name and contact information, including the email address, of the medical professionals who may be associated with the particular patient. For example, the medical professional may be the professional who has requested the study, who is monitoring the study, and/or who is reviewing the study. The medical notes field 75 stores any notes the medical professional has made when reviewing the analysis that has been conducted. The medical information record 76 as described below stores the medical data, along with the results of the analysis.

The date/time field 78 of the medical information record stores the date and time at which a study was undertaken, or the date/time between which a study has been undertaken (for studies that take place over an elapsed period). Each study in the database is identified by a unique reference number. The medical data input field 80 stores the medical data that is based on the detection of the physiological parameters as mentioned above. The output parameters record 82 stores the results of the analysis conducted upon the medical data. The suitable data field 83 is used to store the medical data that is to be used in the analysis. For example, as is described below, the analysis upon the medical data highlights data that is unsuitable for inclusion in subsequent analysis. This may be due to a variety of factors including improper use of the device at a specific period of time. Also, as described below, the user is able to specify periods of time during which medical data was recorded that is unsuitable.

The medical data record 80 is comprised of a blood/oxygen saturation field 84 that stores the blood oxygen saturation levels that have been provided by the medical device 12. The pulse rate field 86 stores the pulse rate that has been detected by the oximeter.

The output parameters record stores the results of the data analysis. In an exemplary embodiment, a desaturation field 92 stores the desaturation measures that have been calculated. The desaturation percentiles field 94 stores the percentiles that have been determined. The $SaO_2$ levels field 96 stores the levels of SaO$_2$ that have been determined from the medical data. The apnea/hypopnea field 99 stores the various apnea and hypopnea related determinations. The determinations include whether there have been any instances of mixed or obstructive apneas, and hypopneans in certain measurements.

The medical data from the medical device 12 is uploaded to the client station 14. The medical data is uploaded after the completion of monitoring a patients physiological parameters, or may continuously provide medical data as the monitoring is being conducted. Medical data that is provided in one upload may represent data that has been collected over a period of time.

Figure 6:
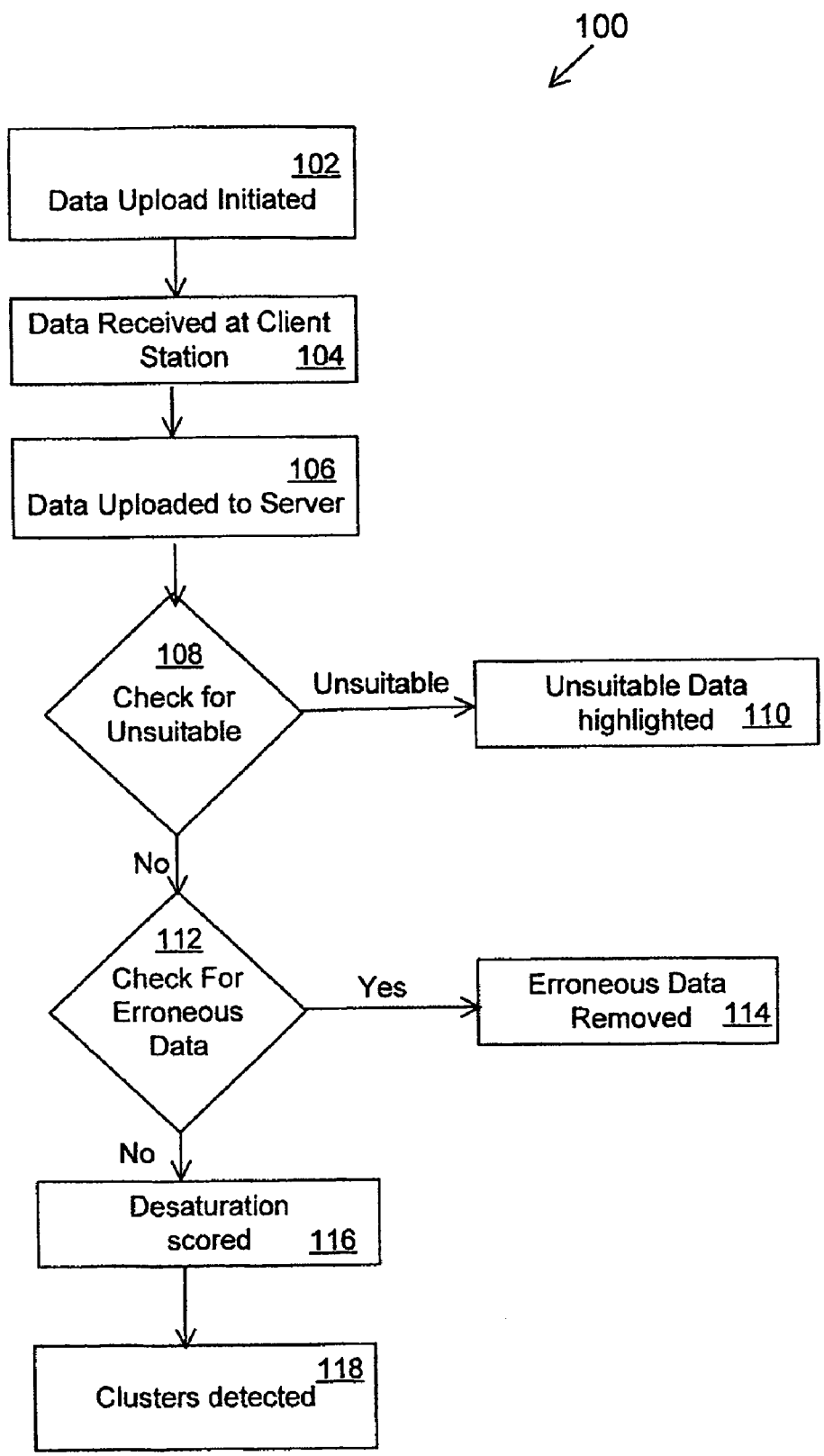
FIG. 6 is a flowchart illustrating the steps of a data upload method.

The transmittal of the medical data (continuous or non-continuous) may be initiated by the user of the medical device 12 when they interface the medical device 12 with the respective client station 14. When the data is received at the client station 14, the session manager proceeds to establish a dedicated session between the client station 14 and the server station 20 through the Internet. Reference is now made to FIG. 6, where the steps of a medical data processing method 100 are shown. The medical data processing method 100 is undertaken when medical data is to be analyzed.

Method 100 begins at step 102, where the transmission of data from the medical device is initiated. The transmission of data is initiated when the device interfaces with the client station 14. At step 104, the medical device data is received at the client station 14. In an exemplary embodiment, the client station 14 temporarily stores a copy of the medical device data that it receives. If the system 10 is server based, at step 106 the medical device data is transmitted from the client station 14 to the server station 20 through the communication network 18. The session manager interacts with the communication application 22. The session manager initiates a session between the server station 20 and the client station 14. In an exemplary embodiment, the session manager may first authenticate the client station 14 and the user of the client station 14 to create a secure session between the client station 14 and the server station 20. The secure session in an exemplary embodiment is a web based session, where data is exchanged between the server station 20 and the client station 14 in an encrypted manner. In an exemplary embodiment, the analysis application, and more specifically, the medical data analyzer will execute one or more medical analysis algorithms. The analysis algorithms determine the presence of output parameters. Based on the output parameters that are determined, one or more visual representations of the study are displayed to the user. The visual representations may include, but are not limited to graphs, charts, records, and reports, and any combination therein. The visual representations of the analysis that are provided to the user, allow users to review the study. For medical devices that are transmitting their data in real time, the analysis is conducted as the medical data is received, and the visual representations are displayed to the user as they are created. When the user is reviewing the visual representation of the study, the user as described below has the ability to specify whether the data that has been included in the study should be classified as unsuitable data. For example, the user may be aware of an instance where the medical device 12 was taking readings and the readings may not have been accurate as the device was not engaged on the patient's body in an appropriate manner.

Upon receiving the medical data, in an exemplary embodiment, a verification process is undertaken to determine the suitability of the medical data for analysis. For example, the data received from the medical device 12 may not be suitable for analysis as it may contain erroneous or otherwise unsuitable data. At step 108, a check is performed to determine the presence of unsuitable data. Unsuitable data is identified by the medical sensor 50 as data that may have been generated under an exception condition. An exception condition may occur where the sensor does not produce data based on readings of physiological parameters and produces them based on other factors that are present. For example, one or more of the following exception conditions may occur when a pulse oximeter is used, the sensor is defective, there is a low perfusion rate, there is interference, the device sensor 50 is off, there is ambient light, the sensor 50 is unrecognized or where there is a low signal. An exception indicating that the sensor is defective may occur where the sensor is not functioning properly. The low perfusion rate exception indicates that the signals from the infrared lights have faded, indicating that the light is not in contact with the skin. The unrecognized sensor exception indicates that the sensor is an incompatible sensor. A low signal exception occurs when the patient has moved during the study. Method 100 is able to determine the presence of these exception conditions based on data from the device 12 as it is identified as containing an exception condition. If at step 108, it is determined that an exception code is present, method 100 proceeds to step 110. At step 110, the data that has been identified as exception code data is highlighted as unsuitable data, and is not used in further processing in an exemplary embodiment.

Method 100 then proceeds to step 112, where a check is performed to determine whether there is any erroneous data present. Erroneous data is determined for any data that is monitored over a period of time. Any increase or decrease in a measured parameter beyond an acceptable threshold in a period of time may be characterized as erroneous data. As the medical device data may represent readings taken of physiological parameters over an extended period of time, the data is analysed to determine whether there are any periods of time where the data reflects a change in value that will generally be considered to have been caused by extraneous circumstances. Using a pulse oximeter as an example, the medical device data received from the oximeter is analyzed at step 112 to determine whether there has been an increase or decrease in the blood saturation levels of over 5% in a predetermined interval (in this exemplary embodiment, 2 seconds). The predetermined intervals may be selected according to a tolerance level. It should be noted that the user of the system 10, including a patient or a medical professional is also able to specify conditions that will identify erroneous data as described below. Step 112 as described with respect to an oximeter is further explained with reference to FIG. 12 below. If at step 112, it is determined that erroneous data is present, method 100 proceeds to step 114, where the erroneous data is classified as unsuitable data.

The medical data analyzer processes the medical device data based on analysis algorithms. The algorithms may be modified by the user or medical professional through an interface, and the data the algorithms operate upon may be specified by the patient or medical professional as described below. The analysis application creates a visual representation to display the results of the analysis of the study to the user or medical professional. A visual representation of the study is created and displayed to the user. The analysis application also generates a report based on the analysis conducted of the study and is described in detail below. Method 100 then proceeds to steps 116 and 118, where desaturations and clusters are detected. The method of detecting desaturations and clusters is described in detail below.

Figure 7:
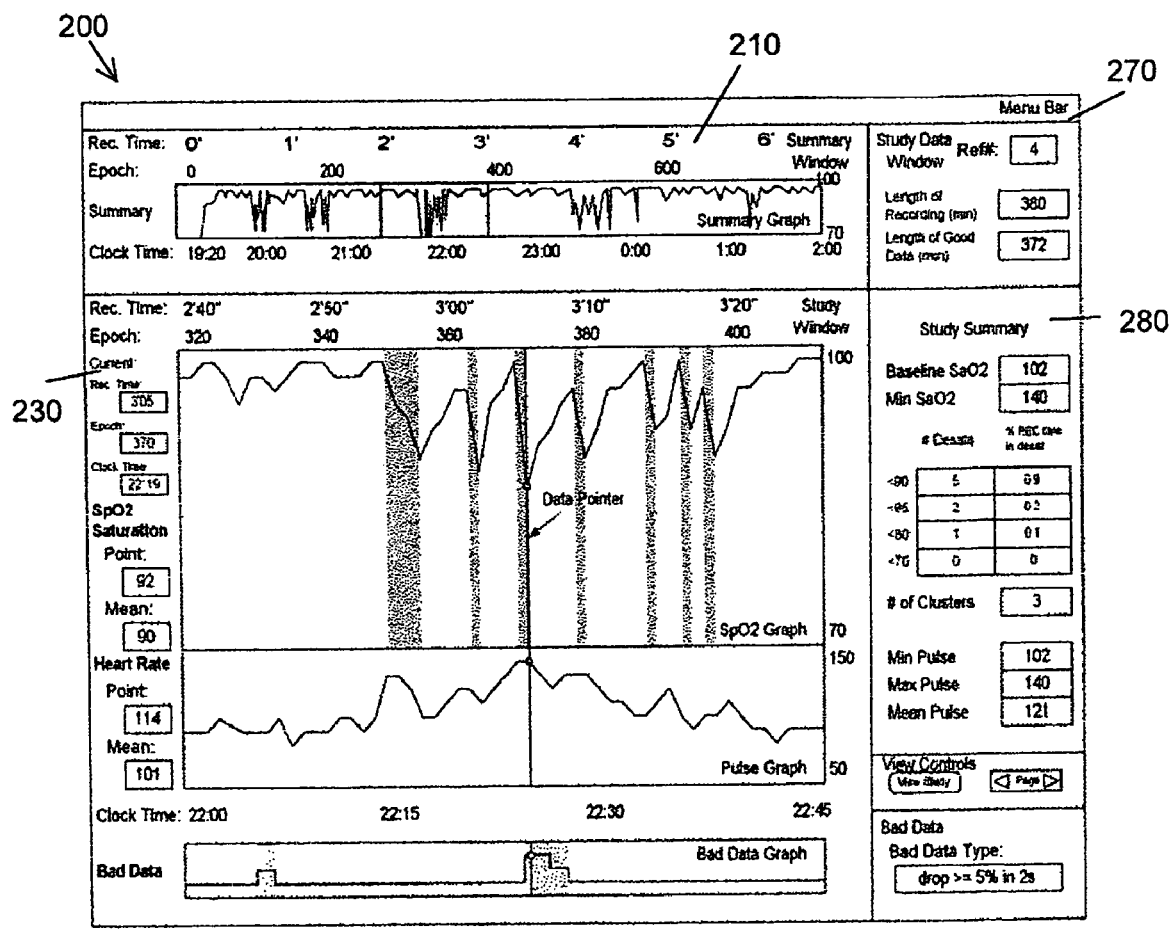
FIG. 7 is a sample illustration of study display window.

Reference is made to FIG. 7, where a sample visual representation that displays the results of the study is shown. A study display window 200 is shown in FIG. 7, and is used to display the results of an oximetry study. The study display window 200 may be created for various types of studies that are based on receiving data from medical devices. The display window 200 in an exemplary embodiment comprises a summary window 210, a study window 230, a study data window 270, and a study summary window 280. The summary window 210 is used to present data related to the whole study. The summary window 230 comprises a graphical representation of the study. The study data window 270 displays a summary of the recording time, a reference to the study, and the length of suitable data. The recording time is the time over which a medical sensor 12 recorded readings of the physiological parameters. The study summary window 280 provides a record of the results of the analysis.

Reference is now made to FIG. 8, where the components of the display window 200 are illustrated in further detail. The summary window 210 and the study window 230 are described with respect to FIG. 8. The summary window 210 comprises a recording time field 212, an epoch time field 214, a summary display graph 216 and a time field 222.

The recording time field 212 displays the number of hours in the study from where the medical device 12 began to measure one or more of the physiological parameters of a patient. The epoch field 214 lists the number of epochs (each epoch is a period of 30 seconds) from the start of the study. The summary display graph 216 provides a graphic representation of the measurements taken during the study. Epochs are recognized units of measurements that are used in sleep analysis. The summary display graph 216 plots the percentage of $SpO_2$ vs. the time and displays the results. In an exemplary embodiment, the time is displayed based on the actual time the readings were taken. The graph highlight window 220 highlights the section of the display window that is shown in further detail in the study window 230. The graph highlight window 220 is specified by the user, depending on the area of the display graph the user wishes to zoom into. The area in the graph window 220 represents visual representations of the entire study. When the user wishes to focus in on a particular area, they can set a beginning and end point of the graph highlight window 220 and have the detailed data shown in the study focus window 222.

The study window 230, in an exemplary embodiment, comprises the following fields, a recording time field 232, an epoch field 234, a current data field 236, a saturation field 238, a heart rate field 240, a time field 242, an unsuitable data window 244, a detailed study graph 246, and one or more desaturation indicators 248. The recording time field 232 displays the number of hours from the start of the study. The epoch field 234 displays the number of epochs (30 second intervals) that are being viewed. The current data field 236 displays the location on the graph of the display pointer, and more specifically displays the recording time associated with the display pointer, the epoch, and the clock time. The display pointer may be moved by the user to any point in the detailed study graph 246. The saturation field 238 displays the saturation level at the point marked by the data pointer, and the mean saturation levels during the study. The heart rate field 240 displays the heart rate at the point marked by the display pointer, and the mean heart rate during the study. A graph is also shown displaying the heart rate during the period of time. The time field 242 displays the time at which the measurements being viewed in the respective windows were taken. The unsuitable data field 244 is used to illustrate the periods of time during the study that periods of unsuitable data have been detected or specified by the user. The desaturation indicators 248 identify any desaturation points that have been identified. The identification of desaturation points is explained in further detail below. In an exemplary embodiment, the desaturation indicators are vertical bars that begin at the beginning of the desaturation period and end at the end of the desaturation period. The user who is viewing the contents of the study graph 246 may zoom into any section of the graph. In an exemplary embodiment, the user may zoom into a particular area by highlighting a section of the graph using their mouse. In alternative embodiments, the user may be provided with the functionality to enter a start time and an end time for a section of the graph they wish to zoom into.

Reference is now made to FIG. 9, where exemplary embodiments of a study data window 270 and a study summary window 280 are shown. The study data window 270, in an exemplary embodiment, displays general information to the user that helps identify the study and the general parameters associated with the study. The study data window in an exemplary embodiment is comprised of a reference number field 272, a length of recording field 274, and length of usable data field 276. The reference number field 272 indicates the reference number that is used to identify the study. The length of recording field 274 indicates the total length of time of the study. The length of usable data field indicates the length of time of the study for which suitable data has been identified.

The study summary window 280 displays a summary of the data that has been analyzed. In an exemplary embodiment, the study summary window 280 comprises a baseline $SpO_2$ field 282, a minimum $SpO_2$ field 284, a desaturation chart 286, a cluster field 288, and a pulse field 290. The baseline $SpO_2$ field 282 displays the calculation of the average $SpO_2$ levels for the entire study (excluding the unsuitable data). The minimum $SpO_2$ field 284 is the minimum $SpO_2$ level that has been detected during the study. The desaturation chart 286 displays the number of desaturations that have been detected in various categories including the number of desaturations below certain points. For example, the chart indicates the number of desaturations below 90, 85, 80, and 70 percent respectively. The desaturation chart also provides, in an exemplary embodiment, the percentage of time that the study was in a state of desaturation. The clusters field 288 indicates the number of clusters that have been detected. The pulse field 290 displays the minimum pulse rate, the maximum pulse rate and the mean pulse rate that were measured during the study.

As has been shown with respect to FIG. 7, the visual representation of a study displays to the patient or medical professional, the results of the analysis conducted. As users of the system 10 are required to sign up to access the system, they will be asked to provide demographic information as part of the sign up process. Various levels of access are given to the system, and various types of users may access the system. For example, medical professionals may be provided with varying levels of access. For example, some medical professionals may have permission to view the studies associated with numerous patients (i.e. those belonging to one medical center or for example those that have a common physician). Also, some medical professionals may be given permission to only view results of the study that are shown in the visual representations, whereas other medical professionals may be given permission to invite others to view the results of the study. As a further example, some medical professionals may view results of studies conducted by a particular medical device or by a group of medical devices that are affiliated with a particular institution. When signing up to use the system, various levels of access and various functionalities are available. A user may sign up to use the system according to various payment methods. The methods of collecting payments for use of the system may vary, and may include pay-per use models, unlimited use licenses, or institutional licenses.

Upon a user logging into the system, the users profile is compared with the parameters associated with the advertisements that are available. For example, when a user is engaging the system to upload medical device data, the user may subsequently be shown advertisements for other medical devices that are available and/or may show advertisements for other goods or services offered by the manufacturer of the medical device.

When a user accesses the system to view a study, advertisements are displayed that are tailored to the demographic profile and study type associated with the users. The advertisements that are displayed to the user are based on a combination of the demographic profile, type of study undertaken and the type and model of medical device being used. For example, with advertisements that are based on the demographic profile, this may take into consideration, the age, sex, location and other such factors associated with the user. The factors taken into account with respect to advertisements, include but are not limited to the type of study, the length of the study, and other such factors. Therefore, advertisements for a specific medical device and its associated components may be displayed to a user who is using that medical device and who is resident in a location where that medical device is available. Also, as an example, if the study was undertaken because of the inability to fall asleep (as was specified by the user, and as recorded in the database) then products and or services that are targeted towards sleep products and/or services may be shown to the user. The advertisements may also be based on a combination of user type and level of access, demographics and where applicable information associated with the study. Each advertisement that may be shown to the user may have associated with it various parameters. The parameters associated with the advertisements may include information that characterizes the company that is offering the goods and/or services, the location of the goods and/or services, the classification of the goods and/or services and what they may be used for.

Figure 10:
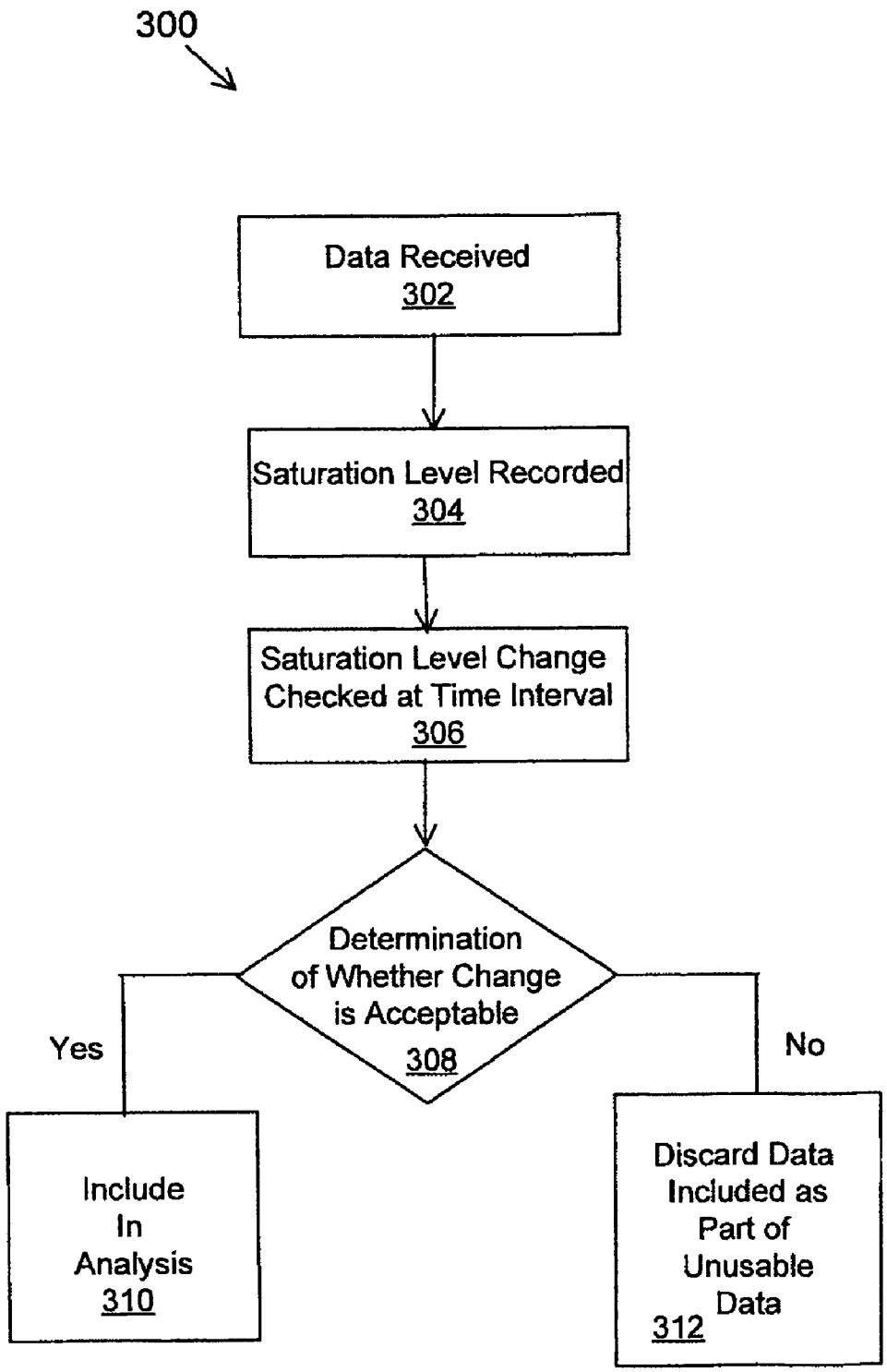
FIG. 10 is a flowchart illustrating the steps of a data detection method.

Reference is now made to FIG. 10, where the steps of a unusable data detection method 300 are shown. Method 300 is described with respect to data that is received from a pulse oximeter. Method 300 begins at step 302, where the medical data is received from the medical device 12. Method 300 then proceeds to step 304 where the oxygen saturation levels are recorded. Method 300 proceeds to step 306, where changes in saturation levels are determined at predefined time intervals. For example, the predefined time interval when studying data from an oximeter is a five second interval in one exemplary embodiment. Method 300 then proceeds to step 308 where a determination is made as to whether the change in saturation level is acceptable based on an acceptable threshold. In an exemplary embodiment, a change of less than 5% every two seconds is acceptable. Increases or decreases of more than 5% every two seconds result in that block of data being classified as unsuitable data. If the check performed at step 308 results in the change in saturation levels (if any) being classified as acceptable, then method 300 proceeds to step 310. At step 310, the data is included in the data set that is analyzed. If at step 308, it is determined that the change in the desaturation level is unacceptable, method 300 proceeds to step 312. At step 312, the data whose change in saturation level is unacceptable, is included in unsuitable data set, and removed from the data set upon which further analysis or calculations are to be conducted.

Figure 11A:
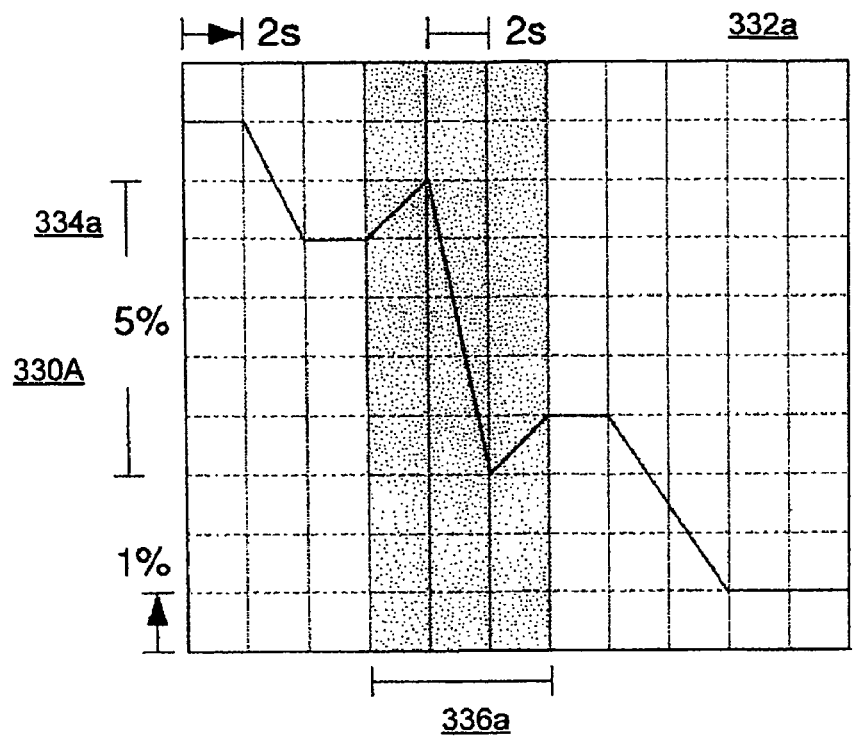
FIG. 11A is a graph of a monitoring graph.
Figure 11B:
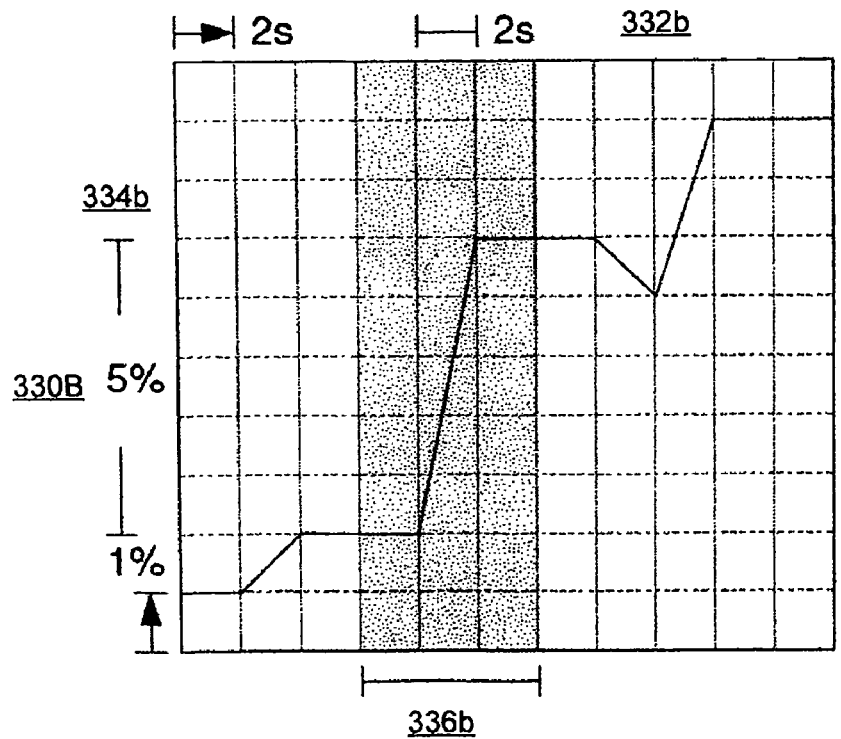
FIG. 11B is a graph of a monitoring graph.

Reference is now made to FIGS. 11A and 11B. FIG. 11A and FIG. 11B illustrate graphs representing the monitoring of the saturation levels. Reference is made to FIG. 11A, where a monitoring graph 330A is shown. The monitoring graph 330A plots the elapsed time 332A vs. the desaturation percentage 334A. The highlighted area 336A indicates an area on the graph where a decrease of saturation levels of 5% has been detected in a two second interval. The entire highlighted area 336a indicates a two second interval before the decrease and a two second interval after the decrease. The data contained in this highlighted area is classified as unsuitable data and is not used in subsequent analysis.

Reference is now made to FIG. 11B, where a monitoring graph 330B is shown. In monitoring graph 330B, the elapsed time 332B is plotted vs. the desaturation percentage 334B. The highlighted area 336B indicates that a desaturation increase of 5% has been detected in a two second interval. The highlighted area 336B also includes the desaturation measures two seconds before, and two seconds after the 5% desaturation increase. This data is marked as unsuitable data and is not used in the subsequent analysis. The determinations as to possible desaturations may also be made by determining whether any plateaus exist. Plateaus indicate a period of little or no change in the blood oxygen levels between desaturations or during a desaturation. The total time of desaturations is determined first, and the plateau is analyzed to determine the existence of a plateau. The total duration of a plateau is compared to the total time associated with the desaturation, to determine if more than one desaturation exists.

Figure 12:
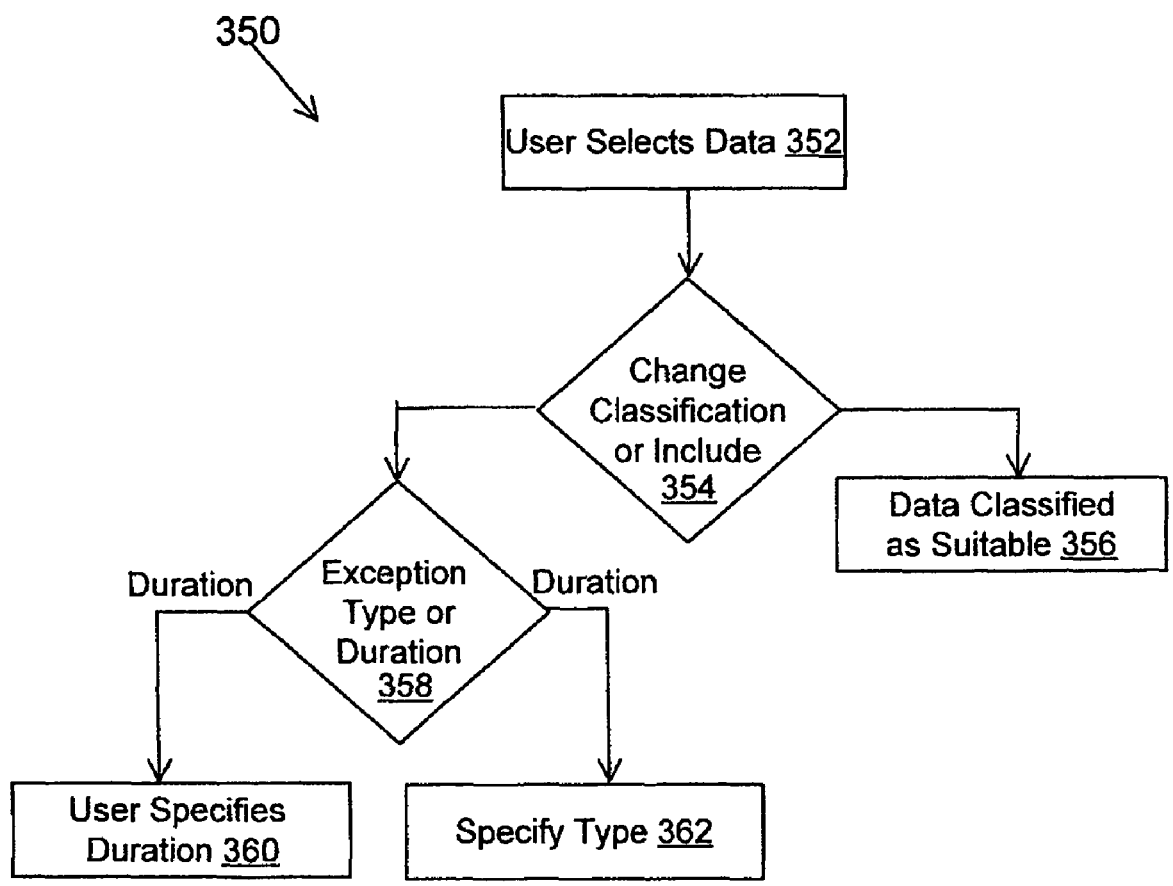
FIG. 12 is a flowchart illustrating the steps of a data review method.

The user of the system 10, once data has been classified as unsuitable is able to review the data that has been classified as unsuitable. Reference is made to FIG. 12, where the steps of a data review method 350 are shown. The review data method 350 presents the user with the option of reviewing the data that has been classified as unsuitable, and for the user to change the classification and/or the reason the data has been classified as unsuitable. Method 350 begins at step 352 where the user selects a set of data from the unsuitable data. In an exemplary embodiment, the unsuitable data set may be displayed in a graph form, where the data is displayed according to the time it was recorded. The user may select one or more sets of data. Upon selecting the unsuitable data, method 350 proceeds to step 354, where the user is presented with the option of changing the classification information associated with the data, or having the data classified as suitable data. If the user chooses to have the data classified as suitable data, method 350 proceeds to step 356, where the data is classified as suitable data. A user may choose to have the data classified as suitable or unsuitable, as there may be debate whether data is suitable or unsuitable. Upon the data being classified as suitable data, the data is used in the analysis. If at step 354, the user specifies that the classification of the data should be changed, method 350 proceeds to step 358. At step 358, the user may select to change the duration for which a particular data set has been classified as unsuitable, or may wish to change the reason for the classification, or both. At step 358, if the user selects to change the duration for which the data has been classified as unsuitable, method 350 proceeds to step 360. At step 360, the user reviews a representation of the data that has been classified as unsuitable, and the user may specify a different start period and a different end period for each set of data that has been classified as unsuitable. If at step 358, the user selects to change the exception type that is associated with the set of unsuitable data, method 350 proceeds to step 362. At step 362, the user is able to specify an exception type that is associated with each set of unsuitable data. For example, the user may chose to select a different exception that is associated with the period of unsuitable data.

Figure 13:
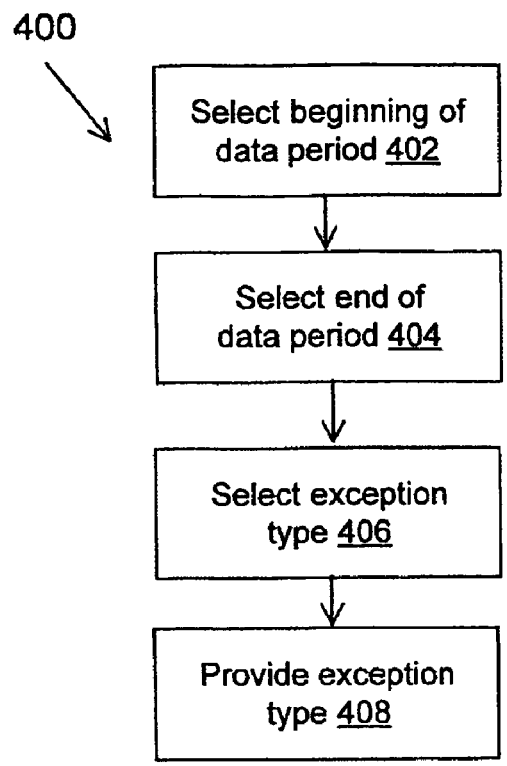
FIG. 13 is a flowchart illustrating the steps of a data classification method.

As has been described above, the user of system 10 is able to review data that has been classified as unsuitable. When reviewing data that has been classified as unsuitable, the user is able to specify that some of the data should be classified as suitable data. Users of the system 10 are also able to review data that has been classified as suitable, to confirm that such data has been classified correctly, and that such data should be included in the analysis. Reference is now made to FIG. 13, where the steps of a data classification method 400 are shown. Data classification method 400 allows a user to view representations of data that have been classified as suitable, and specify whether any data should be classified as unsuitable. When a user wishes to classify data as unsuitable, the user may engage method 400. Method 400 begins at step 402, where a user selects a start period for a period of data that is to be classified as unsuitable data. In an exemplary embodiment, as the representation of the suitable data is shown as a graph, the user may select this period on the graph. In an alternative embodiment the user may enter the beginning time co-ordinate through functionality provided on an interface. Method 400 then proceeds to step 404. At step 404, the user selects an end period for the data being classified as unsuitable. Method 400 then proceeds to step 406, where the user specifies the type of exception associated with the unsuitable data.

Figure 14:
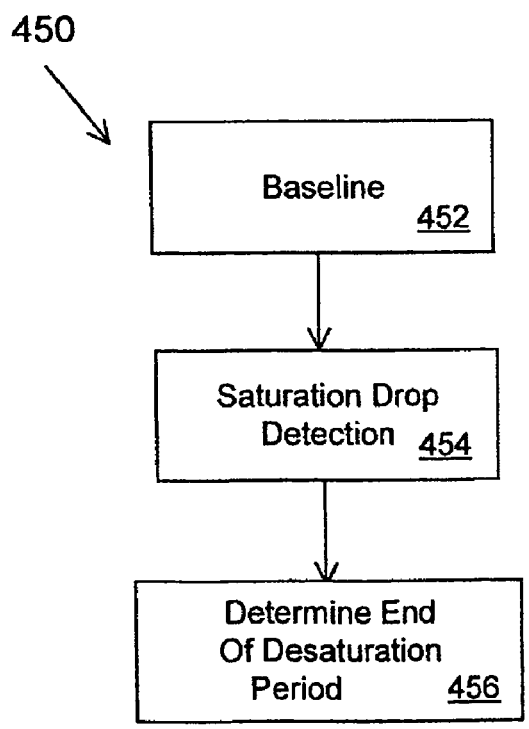
FIG. 14 is a flowchart illustrating the steps of an automated desaturated scoring method.

In an exemplary embodiment, the medical data analyzer when analyzing oximeter data, analyzes the data to determine the number of desaturations that have occurred during a study. Reference is now made to FIG. 14 where the steps of an automated desaturation scoring method 450 are shown. The desaturation scoring method begins at step 452, where a baseline desaturation level is first defined. In an exemplary embodiment, the baseline desaturation level is defined as the highest $Spo_2$ reading over the preceeding ten seconds. It should be noted, that the ten second period has been used only for purposes of example, and other periods of time may be used. As the $SpO_2$ levels are recorded at each instance, the $SpO_2$ levels over the previous ten seconds are checked continuously. Method 450 then proceeds to step 454, where the saturation levels are monitored to detect whether there has been a drop of more than 4%. A drop of more or less than 4% may be used, however, 4% has been used for purposes of this exemplary embodiment. If at step 454, a saturation drop of more than 4% has been detected, method 450 proceeds to step 456. At step 456, the end of the desaturation period is determined. The end of the desaturation period is determined where an increase of 1% is detected. Where an increase of 1% is detected, the desaturation period will have ended. The increase of 1% that has been detected that determines the end of the desaturation, must last for at least 4 seconds in an exemplary embodiment. At the end of method 450, the number of desaturations that have occurred during the study are determined. Method 450 has described the method used in an exemplary embodiment where the analysis application analyzes the medical data. Upon the determination of the number of desaturations by the analysis application, the user is able to review and edit the results.

Figure 15:
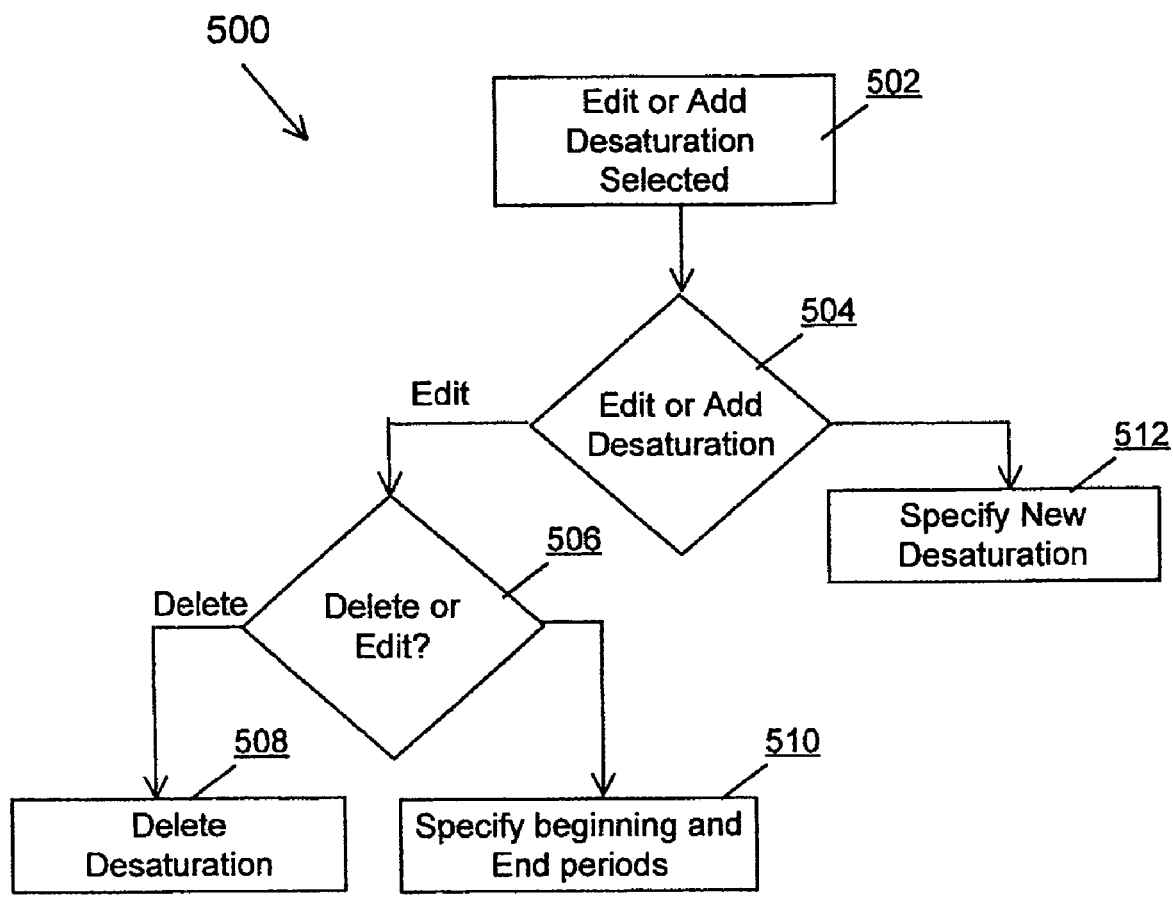
FIG. 15 is a flowchart illustrating the steps of a desaturation review method.

Reference is made to FIG. 15, where the steps of a desaturation review method 500 are shown. The desaturaton review method 500 provides the user with the ability to review the desaturations that have been determined by the analysis application 16 and to edit the beginning and end periods of any desaturations that have been determined, or to specify new desaturations. Reference is made to again to FIG. 8, where the desaturation indicators 248 represent the desaturations that have been detected. In method 500 the user engages the desaturation indicators 248 to specify different beginning and end periods for the desaturations. Method 500 begins at step 502, where the user chooses to edit or add desaturations from a menu that has been provided. Method 500 then proceeds to step 504. At step 504, the user may either choose to edit a defined desaturation or to add a desaturation. Method 500 proceeds to step 506 where the user chooses to edit a desaturation. When a user chooses to edit a desaturation, the user may either change the beginning and end periods of the desaturation, or delete the desaturation that has been identified. Method 500 proceeds to step 508 when the user chooses to delete a desaturation. In an exemplary embodiment, the user may delete a desaturation by selecting the desaturation indicator 248. When the desaturation indicator 248 is selected, the user is presented with the option of deleting the desaturation. In alternative embodiments, the desaturations presented to the user may have a reference number associated with them, and the user may select to delete the desaturation through specifying the reference number of the desaturation they wish to delete. If at step 508, the user selects the option of editing the desaturation, method 500 proceeds to step 510. At step 510, the user specifies new beginning and end periods for the desaturation. If at step 504, the user selects the option of adding a desaturation, method 500 proceeds to step 512. At step 512, the user specifies beginning and end periods for new desaturations points.

The medical data analyzer based on the determination of the number of desaturations also determines the existence of clusters in an oxymetry study. The data analyzer, in an exemplary embodiment determines whether there have been five or more desaturations in a period of less than 30 minutes. In order to differentiate between clusters, an interval of 45 minutes is specified in an exemplary embodiment, between the end of one cluster and the start of another cluster.

Where the user has made any additions or has edited the results of the analysis that has been conducted this data is saved to the analysis database 68. The user defined or edited data is saved, and the users of the system 10 who are reviewing the study are always given the option of reviewing the results of the analysis without the user defined or edited data, or with the user defined and edited data.

When a study has been completed, the analysis application provides a report generation functionality. The user, in an exemplary embodiment will specify the type of study that is being uploaded. For example, with reference to studies that are conducted by the oximeter, the user may specify the exact type of study, which may include but is not limited to, an abbreviated oximetry study, a polysomnography study, a six minute walk test, and the ninety minute child sleep test. The report summarizes the analysis that has been conducted of the study, and may include the visual representations that were shown to the user. As a study generally will have a medical professional associated with it, once a study has been completed, the report of the study is automatically generated and sent to the medical professional. In an exemplary embodiment, the medical professional receives an email indicating that the report is ready for viewing, or will receive an email with the report attached. Also, where the medical professional has associated with it a clinic/hospital or other such institution that the patient is associated with, the report is generated and sent electronically to an address associated with the clinic/hospital or other such institution. When a user accesses the system 10, they are presented with the option of viewing all of the past reports that they are associated with, either as a patient, or as a medical professional. The user may customize reports that they wish to generate. For example, the user may specify upon the interface associated with the application, that a report be generated that comprises specific data.

As medical professionals will review the results of the analysis, the system 10 provides for functionality where the medical professional or patient may share the results of the study and or the reports with others. The analysis of the study, and the reports may be sent to others at the discretion of those users with the appropriate level of access. An email notification may be sent by one medical professional to another medical professional to review a study. The system 10 allows multiple users to concurrently view the results of the study. The user who requests that other users view the visual representations of a study, may provide the requested users with limited access to the study. Also, the system 10 provides for notification capabilities. For example, a medical professional can specify that they wish to receive an email notification when a study associated with a particular patient has been analyzed.

As has been mentioned above, the methods and systems that have been described above may be used to provide analysis of data from any medical devices. An oximeter has been used for purpose of example only.

The present invention has been described with regard to exemplary embodiments. However, it will be obvious to persons skilled in the art that a number of variants and modifications can be made without departing from the scope of the invention as described herein.

The invention claimed is:

1. A system for analyzing medical data, the system comprising:
   a server adapted to be connected to a communication network for storing physiological parameters of a patient over a period of time, wherein the physiological parameters are generated by a medical device, wherein the medical device is a pulse oximeter;
   a session manager for establishing a session for a user to communicate with the server;
   a data manager connected to the session manager, wherein the data manager allows for storage of the physiological parameters and providing access to previously stored physiological parameters; and
   a medical data analyzer connected to the data manager for:
      (i) classifying the physiological parameters as one of suitable and unsuitable for analysis;
      (ii) analyzing at least one suitable physiological parameter over the period of time to produce analysis results; and
      (iii) providing visual representations of the analysis results, wherein the visual representations identify the at least one suitable physiological parameter and at least one unsuitable physiological parameter, wherein the visual representations are based on physiological parameters analysis algorithms.

2. The system as claimed in claim 1, wherein the visual representations may be any combination of graphs, charts, records, tables, and reports.

3. The system as claimed in claim 1, wherein the system may be accessed through a communication network.

4. The system as claimed in claim 3, wherein the communication network is the internet.

5. The system as claimed in claim 1, wherein the system may is adapted to be accessed by patients and medical professionals.

6. The system as claimed in claim 5, wherein the medical data analyzer accepts input from patients and medical professionals when analyzing the physiological parameters.

7. The system as claimed in claim 1, further comprising a computing station adapted to be connected to the medical device.

8. The system as claimed in claim 7, wherein the medical device uploads physiological parameters to the computing station, wherein the computing station then transmits the uploaded physiological parameters to the server.

9. The system as claimed in claim 7, wherein the medical data analyzer is distributed between the computing station and the server.

10. The system as claimed in claim 7, wherein the session manager is distributed between the computing station and the server.

11. A system for analyzing physiological parameters, the system comprising:
    a medical device recording physiological parameters from a patient over a period of time;
    a computing station, wherein the medical device uploads the physiological parameters to the computing station;
    a server connected to a communication network for storing the physiological parameters;
    a data manager associated with the medical device for establishing an authenticated session over the communication network with the server to enable the server to control further use of the physiological parameters; and
    a medical data analyzer having at least one component associated with the server to allow a medical professional controlled access to the physiological parameters, wherein the medical data analyzer:
       classifies the physiological parameters as one of suitable and unsuitable for analysis; and
       analyzes at least one suitable physiological parameter over the period of time.

12. The system of claim 11, wherein the medical data analyzer is distributed between the computing station and the server.

13. The system of claim 11, wherein the medical professional requests authentication from the server to have controlled access to the physiological parameters.

14. The system of claim 11, wherein the medical professional may collaborate with one or more other medical professionals to view the physiological parameters.

15. The system of claim 11, wherein the medical data analyzer accepts input from the medical professional when analyzing the physiological parameters.

16. A system for analyzing medical data, the system comprising:
    a server adapted to be connected to a communication network for storing physiological parameters of a patient over a period of time, wherein the physiological parameters are generated by a pulse oximeter;
    a session manager for establishing a session for a user to communicate with the server;
    a data manager connected to the session manager, wherein the data manager allows for:
       (i) storage of the physiological parameters, wherein the physiological parameters define at least one desaturation period; and
       (ii) access to the physiological parameters previously stored on the server; and
    a medical data analyzer connected to the data manager for analyzing the physiological parameters over the period of time, wherein analyzing the physiological parameters comprises:
       (i) determining the number of desaturation periods in the period of time; and
       (ii) determining the existence of at least one cluster based on the number of desaturation periods.

17. The system of claim 16, wherein determining the number of desaturation periods comprises:
    (i) establishing a baseline desaturation level from the physiological parameters;
    (ii) detecting a beginning point of a desaturation period when the physiological parameters drop by at least a first predetermined percentage below the baseline desaturation level; and
    (iii) detecting an end point of the desaturation period when the physiological parameters rise by at least a second predetermined percentage.

* * * * *